(12) United States Patent
Suh et al.

(10) Patent No.: US 8,540,957 B2
(45) Date of Patent: Sep. 24, 2013

(54) METHOD FOR PREPARING MICROTUBULAR HALLOYSITE NANOPOWDERS

(75) Inventors: Yong Jae Suh, Daejeon (KR); Young Mi Heo, Anseong Si (KR); Dae Sup Kil, Daejeon (KR); Sung Wook Cho, Daejeon (KR)

(73) Assignee: Korea Institute of Geoscience and Mineral Resources, Daejeon (KR)

( * ) Notice: Subject to any disclaimer, the term of this patent is extended or adjusted under 35 U.S.C. 154(b) by 338 days.

(21) Appl. No.: 12/954,878

(22) Filed: Nov. 28, 2010

(65) Prior Publication Data

US 2012/0107214 A1    May 3, 2012

(30) Foreign Application Priority Data

Oct. 28, 2010    (KR) .......................... 10-2010-0105658

(51) Int. Cl.
*C01B 33/26*    (2006.01)

(52) U.S. Cl.
USPC ..................................... 423/328.1; 423/328.2

(58) Field of Classification Search
USPC ............................................ 423/328.1, 328.2
See application file for complete search history.

(56) References Cited

U.S. PATENT DOCUMENTS 7,888,419 B2 *    2/2011    Cooper et al. ................ 524/445

* cited by examiner

*Primary Examiner* — Stuart Hendrickson
(74) *Attorney, Agent, or Firm* — Kile Park Reed & Houtteman PLLC

(57) ABSTRACT

The present invention provides a method for preparing microtubular halloysite nanopowders by cutting halloysite nanotubes at a high pressure, microtubular halloysite nanopowders prepared by the method, and a cosmetic composition comprising the microtubular halloysite nanopowders. According to the method of the present invention, it is possible to prepare the halloysite nanopowders with a tubular shape using natural halloysite and effectively select a halloysite nanopowder having a desired shape. The microtubular halloysite nanopowders can be used in many industrial fields and used as a container or a carrier for nanoparticles or organic materials such as drugs, air fresheners, cosmetics, agricultural chemical materials, etc.

8 Claims, 10 Drawing Sheets

(a)

000# METHOD FOR PREPARING MICROTUBULAR HALLOYSITE NANOPOWDERS

CROSS-REFERENCE TO RELATED APPLICATION

This application claims priority to and the benefit of Korean Patent Application No. 10-2010-0105658, filed on Oct. 28, 2010, the disclosure of which is incorporated herein by reference in its entirety.

BACKGROUND

1. Field of the Invention

The present invention relates to a method for preparing microtubular halloysite nanopowders and, more particularly, to a method for preparing microtubular halloysite nanopowders by cutting halloysite nanotubes at a high pressure, microtubular halloysite nanopowders prepared by the method, and a cosmetic composition comprising the microtubular halloysite nanopowders.

2. Description of the Related Art

Halloysite, a kind of natural clay mineral, is an aluminosilicate mineral with a 1:1 layer structure consisting of a tetrahedral silica layer, an octahedral alumina layer, and a layer of water molecules situated between the two layers. Most halloysites are natural minerals in the form of long tubes having an aspect ratio of 10 or more and are called "nanotubes" as they have an inner diameter of about 10 to 15 nm.

Halloysite nanopowders can be used as a container or carrier of nano sized particles or organic materials such as drugs, cosmetics, etc. Moreover, the halloysite nanopowders are environmentally-friendly nanomaterials that can maintain the efficacy for a long time, and thus the halloysite nanopowders can be used as high value-added materials in many industrial fields.

However, the natural halloysite has a long tube-like shape, and thus if it is injected into a blood vessel, it may damage cells. Moreover, if it is used as a cosmetic, it causes irritation to the skin or it makes it difficult to achieve a soft feel. To solve these problems, a technique for preparing halloysite nanopowders having a length of several micrometers with a tubular shape that can contain the contents is required.

Meanwhile, the halloysite has a diameter of 30 to 250 nm and a length of 0.2 to 40 μm, and thus it is difficult to separate the nanoparticles using conventional mineral separation techniques. For example, the sieving can be done up to several microns, and an effective filtration for solid-liquid separation cannot be effectively used for solid-solid separation. While commercially available apparatuses using a cyclone principle can effectively separate powders of 1 μm or less from powders having a particle size greater than 1 μm, it is not known whether they can be used to separate rod-like powders, and further it is difficult to separate submicron-sized powders.

In addition, there are many conventional techniques for separating nanoparticles ranging from several tens of microns to submicron size, such as field-flow fractionation (FFF), hydrodynamic chromatography (HDC), capillary hydrodynamic fractionation (CHDF), split-flow thin (SPLITT) fractionation, and pinched flow fractionation (PFF). However, these conventional techniques are aimed at separating blood components, and there are many problems that a complicated external device for particle injection is required, and it takes a lot of time to ensure accurate separation. Therefore, a technique for separating and selecting mineral powders in large quantities is required.

Recently, there is extensive research that pays attention to carbon nanotubes serving as a carrier for microparticles and aims at using the carbon nanotubes. However, a method for effectively cutting natural halloysite to have a length of several micrometers with a tubular shape has not been reported so far.

Therefore, the inventors of the present invention have made extensive efforts to develop a method for ultra-fine grinding natural halloysite to a short length and selecting halloysite nanopowders having an appropriate size according to the application field and, as a result, have confirmed that it is possible to prepare a halloysite having a length of several micrometers and maintaining the tubular shape by using a method of cutting halloysite nanotubes at a high pressure and a method of selecting halloysite nanopowders using a continuous centrifuge, thereby completing the present invention.

SUMMARY OF THE INVENTION

The present invention has been made in an effort to solve the above-described problems associated with the prior art, and an object of the present invention is to provide a method for preparing microtubular halloysite nanopowders, comprising cutting halloysite nanotubes at a high pressure.

Another object of the present invention is to provide microtubular halloysite nanopowders prepared by the above-described method.

Still another object of the present invention is to provide a cosmetic composition containing the microtubular halloysite nanopowders.

In one aspect, the present invention provides a method for preparing microtubular halloysite nanopowders, the method comprising cutting halloysite nanotubes at a high pressure.

The term "halloysite" used in the present invention means a natural clay mineral such as an aluminosilicate mineral with a 1:1 layer structure consisting of a tetrahedral silica layer, an octahedral alumina layer, and a layer of water molecules situated between the two layers and means a natural mineral in the form of a long tube having an aspect ratio of 10 or more. To use the halloysite as a cosmetic base, it is necessary to provide halloysite nanopowders having a uniform particle size and, as the feeling of use is improved when the particle size is smaller, the halloysite nanopowders can be used as an advanced cosmetic material.

Accordingly, the method for preparing the microtubular halloysite nanopowders may comprise cutting halloysite nanotubes at a high pressure of 15,000 to 25,000 psi, preferably 18,000 to 22,000 psi, more particularly 20,000 psi.

The step of cutting the halloysite nanotubes at a high pressure may comprise continuously grinding the halloysite nanotubes 3 to 9 times.

According to a detailed embodiment of the present invention, a colloid solution having a concentration of 3% was prepared by dispersing the halloysite nanotubes in distilled water, and the resulting solution was ground at a pressure of 10,000 to 30,000 psi using a microfluidizer 3 to 48 times. As a result, it can be seen that the halloysite nanotubes in a flake shape were prepared when the halloysite nanotubes were ground at a pressure of 20,000 psi 24 times (refer to FIG. 2). Moreover, the characteristic peaks of the halloysite nanopowders almost disappeared when the halloysite nanotubes were ground at a pressure of 30,000 psi 24 times, and thus the crystal structure was destroyed (refer to FIG. 3). Furthermore, while halloysite nanopowders having a particle size of 5 μm or less were prepared when the halloysite nanotubes were ground at a pressure of 20,000 psi 12 times, the volume fraction was reduced (refer to FIG. 7). Therefore, the present inventors have found that it is possible to obtain halloysite nanopowders having a particle size of 10 μm or less with a tubular shape when the halloysite nanotubes are ground at a pressure of 15,000 to 25,000 psi 3 to 9 times and actually found this when the halloysite nanotubes are ground at a pressure of 20,000 psi 6 times.

According to the present invention, the halloysite nanopowders have a length of 1 to 10 μm, preferably 1 to 5 μm, and still maintain the tubular shape, instead of a chip or flake shape, even after the cutting procedure. The length and shape of the halloysite nanopowder is suitable for containing cosmetic materials, drugs, agricultural chemical materials, etc., and thus the halloysite nanopowder can be used as a container or a carrier.

The method for preparing the microtubular halloysite nanopowders may further comprise selecting halloysite nanopowders having a desired shape from the cut halloysite nanotubes using a continuous centrifuge.

The term "centrifuge" used in the present invention means a machine most widely used to separate a homogenate into different parts using a centrifugal force. That is, the centrifuge is a device that can separate materials from one another according to the particle size and density of nanoparticles when the homogenate is placed in a centrifuge tube and rotated at a high speed.

To solve the conventional problem that it is difficult to effectively separate small nanoparticles from large ones using a typical batch-type centrifugation method, the present invention employs a continuous centrifugation method. For example, a continuous centrifuge with a rotational speed of 16,000 rpm and a flow rate of 1,200 L/h, which can apply a centrifugal force that is 15,800 times the force of gravity, may be used.

The step of selecting the halloysite nanopowders may comprise lining a centrifuge tube with a Teflon sheet to easily collect nanoparticles and operating the centrifuge. After the solid and liquid phases are separated by the centrifuge, the halloysite nanopowders can be selected by dividing the solid content from an inlet of the centrifuge at predetermined intervals. The predetermined intervals can be determined by considering the size of the nanoparticles. As a result of selecting the nanopowders by the above-described method, it can be found that the nanopowders having a desired length with the tubular shape can be simply and effectively selected.

According to a detailed embodiment of the present invention, a 10 wt % (200 g/2 L) halloysite suspension was stirred for about 1 hour to be subjected to ultrasonic treatment, and the resulting suspension was passed through a microfluidizer at a pressure of 20,000 psi 6 times and then diluted to 1 wt % while maintaining the pH of the suspension at 10. Then, the solid and liquid phases were separated by the centrifuge and sampled (flow rate 6 lpm; centrifugal speed 5,200 rpm) by dividing the solid content from the inlet of the centrifuge at intervals of 14 cm. As a result, it can be found from the samples collected on the Teflon sheet in the region up to 28 cm from the inlet that it was possible to collect nanopowders having a particle size of 0.3 μm or more at a yield of 59.4% (31.6%+27.8%) (refer to FIG. 13).

During the selection of the halloysite nanopowders, the halloysite nanopowders having a length of 1 to 10 μm, preferably 1 to 5 μm, with the tubular shape may be selected.

In another aspect, the present invention provides microtubular halloysite nanopowders prepared by the above-described method.

The halloysite nanopowders according to the present invention have a length of 1 to 10 μm with a tubular shape.

The halloysite nanopowders according to the present invention maintain the tubular shape, instead of a chip or flake shape, and thus the halloysite nanopowders can contain or carry nano sized particles or material such as drugs, cosmetics, etc. Moreover, since the halloysite nanopowders have a length of 1 to 10 μm, the halloysite nanopowders can be injected into a blood vessel or used as a cosmetic without causing irritation to the skin. Furthermore, the halloysite nanopowders according to the present invention can be used as high value-added environmentally-friendly nanomaterials in many industrial fields and, when the halloysite nanopowders are used as a container or carrier for drugs, cosmetics organic materials, the efficacy can be maintained for a long time.

In still another aspect, the present invention provides a cosmetic composition comprising the microtubular halloysite nanopowders.

The term "cosmetic composition" used in the present invention means a composition containing the microtubular halloysite nanopowders, and the composition can be provided in any formulation. Examples of the formulations of the cosmetic composition may include, but not limited to, creams, packs, lotions, skin lotions, essences, foundations, make-up bases, etc. In more detail, the formulations of the cosmetic composition may include, but not limited to, softening lotions, moisturizing lotions, essences, nourishing lotions, nourishing creams, eye creams, massage creams, sun creams, cleansing creams, powders, foundations, make-up bases, packs, etc. To achieve the object of the present invention, the cosmetic composition can be prepared in any of the above formations and the invention is not limited to the above examples. Moreover, the cosmetic composition according to the present invention can be formulated by typical cosmetic preparation methods.

Moreover, the cosmetic composition of the present invention may comprise typical ingredients used in skin cosmetics in a necessary amount.

In detail, the cosmetic composition of the present invention may further comprise a transdermal penetration enhancer. The term "transdermal penetration enhancer" used in the present invention means a composition that allows a desired ingredient to penetrate cells in a blood vessel at a high absorption rate. Preferably, the transdermal penetration enhancer may include, but not limited to, phospholipids, liposomes, etc., which are used in lecithin cosmetics.

The cosmetic composition of the present invention may further comprise at least one oil phase component selected from the group consisting of vegetable oil, mineral oil, silicon oil, and synthetic oil. In more detail, the oil phase component may include, but not limited to, mineral oil, cyclomethicone, squalane, octyldodecyl myristate, olive oil, vitis vinifera seed oil, macadamia nut oil, glyceryl octanoate, castor oil, ethylhexyl isononanoate, dimethicone, cyclopentasiloxane, sunflower seed oil, etc.

Moreover, the cosmetic composition of the present invention may further comprise a surfactant or a higher alcohol in an amount of 0.1 to 5 wt % to improve emulsification properties. Preferably, it is possible to use typical surfactants such as nonionic surfactants, anionic surfactants, cationic surfactants, amphoteric surfactants, phospholipids, etc.

Furthermore, a water phase component may be used to control the viscosity or hardness of water phase. Preferably, the cosmetic composition of the present invention may further comprise at least one viscosity increasing agent selected from the group consisting of carbomer, xanthan gum, bentonite, magnesium aluminum silicate, cellulose gum, and dextrin palmitate in an amount of 0.001 to 5 wt %.

In addition, the cosmetic composition of the present invention may further comprise medicinal ingredients such as higher fatty acids, vitamins, etc., a sunblock, an antioxidant (such as butylhydroxyanisole, gallic acid propyl, erythorbic acid, tocopheryl acetate, butylated hydroxytoluene, etc.), a preservative (such as methylparaben, butylparaben, propylparaben, phenoxyethanol, imidazolidinyl urea, chlorphenesin, etc.), a coloring agent, a pH adjusting agent (such as triethanolamine, citric acid, sodium citrate, malic acid, sodium malate, fumaric acid, sodium fumarate, succinic acid, sodium succinate, sodium hydroxide, dibasic sodium phosphate, etc.), a humectant (such as glycerin, sorbitol, propylene glycol, butylene glycol, hexylene glycol, diglycerin, betaine, glycereth-26, methyl gluceth-20, etc.), and a lubricant.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Hereinafter, exemplary embodiments of the present invention will be described in detail below with reference to the accompanying drawings such that those skilled in the art to which the present invention pertains can easily practice the present invention.

EXAMPLE 1

Ultra-Fine Grinding Process of Halloysite Nanotubes Using a Microfluidizer

According to the present invention, to finely grind halloysite nanotubes at a high pressure to have a predetermined length with a tubular shape, the halloysite nanotubes were dispersed in distilled water to prepare a colloidal solution at a concentration of 3%, and this solution was injected to an inclined wall at a pressure of 10,000 to 30,000 psi using a microfluidizer such that the halloysite nanotubes were finely ground to a submicron size.

The particle sizes of the obtained products were measured using an optical particle size distribution analyzer employing laser light scattering (Malvern Mastersizer 2000) to obtain the particle size distributions with respect to the number of passes through the microfluidizer. The halloysite nanoparticles have a tubular structure, in which the outer surface comprises a silica component and the inner wall comprises an alumina component, and thus the halloysite nanoparticles have a negative zeta potential near a pH of 7. Moreover, when the halloysite nanotubes are ground to a plate shape, instead of the tubular shape, the charges have opposite polarities, and thus the halloysite nanoparticles agglomerate together. To prevent this, the halloysite dispersion solution was titrated with 0.1 M NaOH to a pH of 10, which is somewhat higher than the point of zero charge of alumina (pH 9.5), and thus both sides of the plate-like halloysite nanoparticles have a negative charge.

In the following tests, the shapes, crystal structures, and average particle sizes of the halloysite nanoparticles were measured at various pressures with respect to the number of passes.

Figure 1:
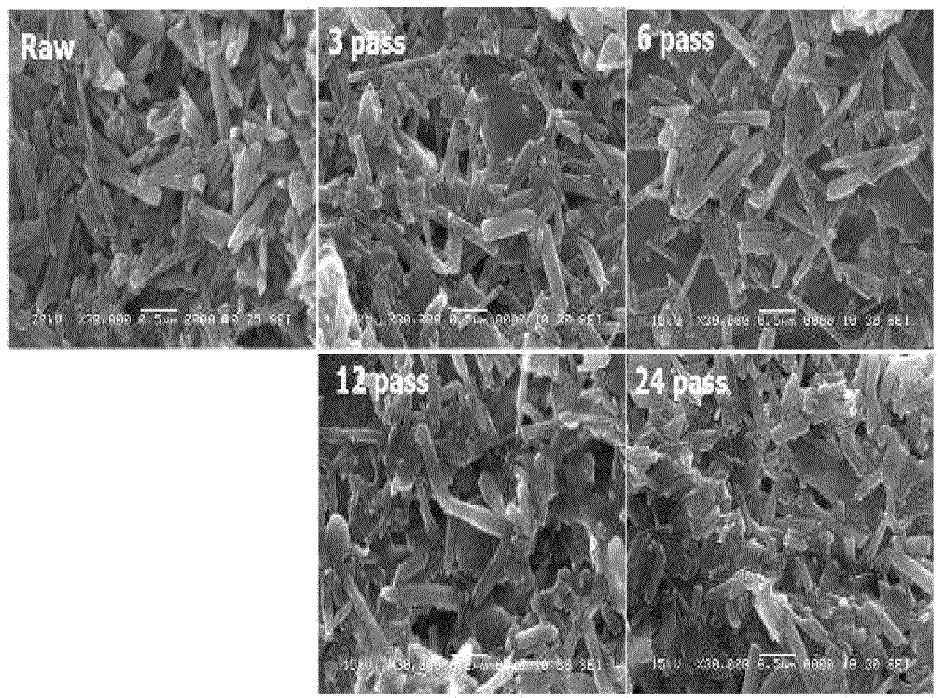
FIG. 1 shows SEM images of halloysite nanoparticles obtained after passing a 3% halloysite colloidal solution through a microfluidizer at a pressure of 20,000 psi by an ultra-fine grinding process with respect to the number of passes.

Analysis of the Shapes of Halloysite Nanoparticles with Respect to the Number of Passes at Various Pressures Through the SEM images of the halloysite nanoparticles obtained after passing a 3% halloysite colloidal solution through a microfluidizer at a pressure of 20,000 psi 24 times by an ultra-fine grinding process with respect to the number of passes, it can be seen that the number of finely ground submicron particles was gradually increased when the number of passes was increased (refer to FIG. 1).

Figure 2:
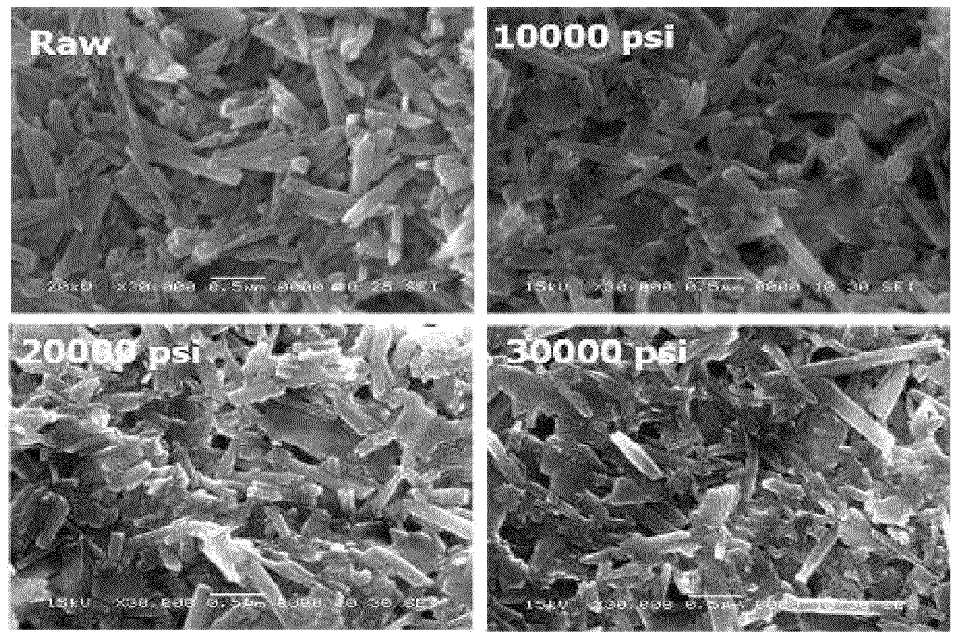
FIG. 2 shows SEM images of halloysite nanoparticles obtained after passing a 3% halloysite colloidal solution through a microfluidizer 24 times by an ultra-fine grinding process in which the pressure was increased from 10,000 psi to 30,000 psi.

Moreover, through the SEM images of the halloysite nanoparticles obtained after passing the 3% halloysite colloidal solution through the microfluidizer 24 times while increasing the pressure from 10,000 psi to 30,000 psi, it can be seen that the grinding efficiency was increased when the pressure was higher, but most halloysite nanoparticles were changed into flake-like nanoparticles (refer to FIG. 2).

This means that the pressure should be reduced as much as possible to maintain the tubular shape because a lot of flake-like nanoparticles are formed when the pressure is higher during the ultra-fine grinding process of the halloysite nanotubes using the microfluidizer.

Figure 3:
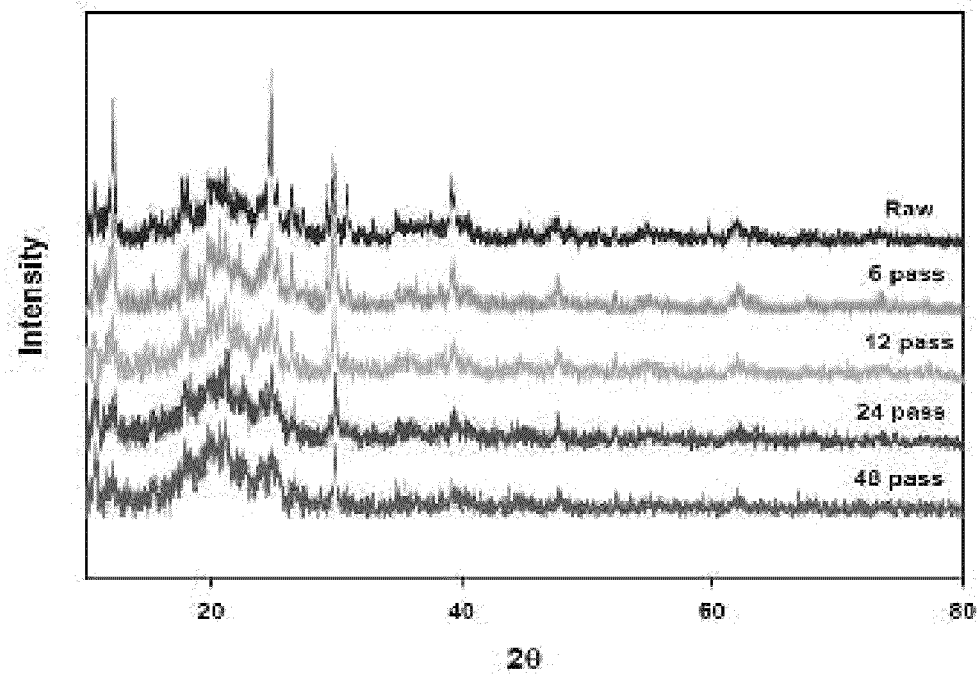
FIG. 3 shows XRD patterns of crystal structures of halloysite nanoparticles at a pressure of 30,000 psi with respect to the number of passes.

Analysis of the Crystal Structures of Halloysite Nanoparticles at Various Pressures with Respect to the Number of Passes The XRD patterns were analyzed to determine the crystal structures of the halloysite nanoparticles obtained from each process, and it can be seen that the crystallinity was reduced when the number of passes through the microfluidizer at a pressure of 30,000 psi was increased and the characteristic peaks of the halloysite nanoparticles almost disappeared after passing 24 times (refer to FIG. 3).

Figure 4:
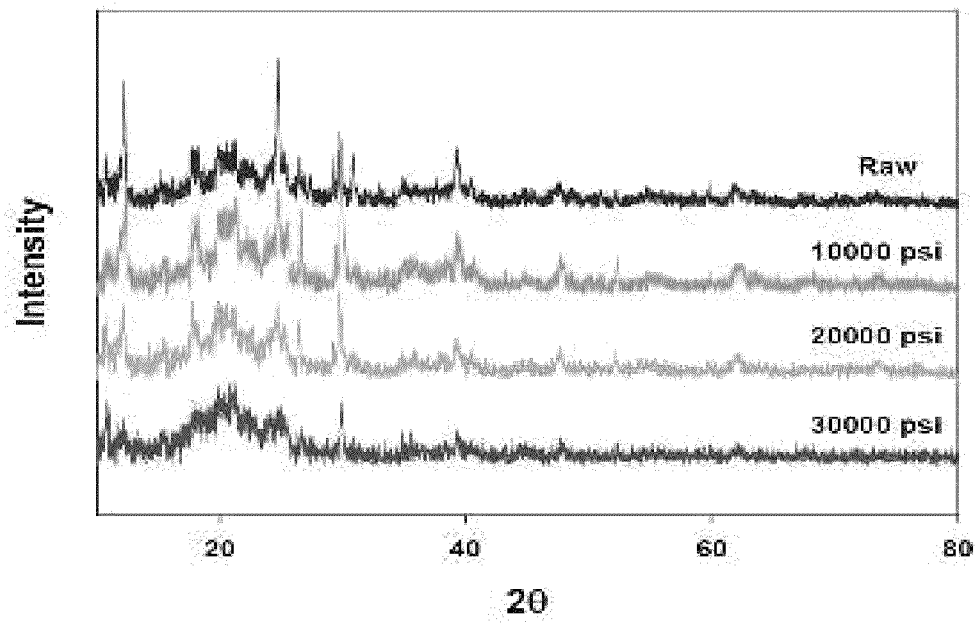
FIG. 4 shows XRD patterns of crystal structures of halloysite nanoparticles obtained after passing a 3% halloysite colloidal solution through a microfluidizer 48 times by an ultra-fine grinding process in which the pressure was increased from 10,000 psi to 30,000 psi.
Figure 5:
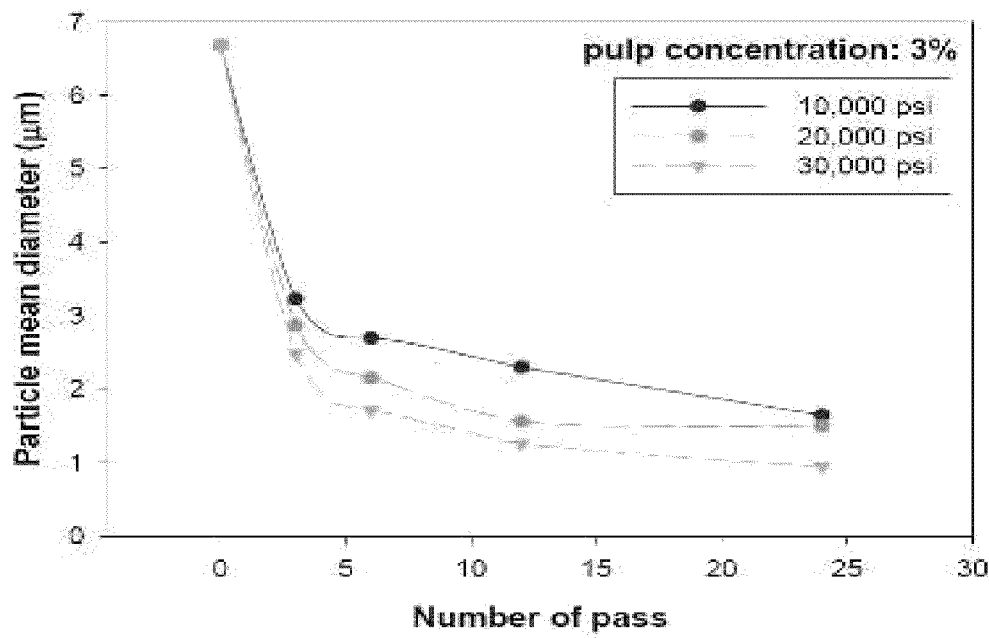
FIG. 5 shows the average particle size distributions of halloysite nanoparticles at each pressure with respect to the number of passes.

This means that the crystal structures were destroyed when the halloysite nanotubes were ground into a flake shape similar to a non-crystal structure. The XRD patterns of the halloysite nanoparticles, obtained after passing the 3% halloysite colloidal solution through the microfluidizer 48 times at a pressure of 10,000 psi to 20,000 psi, respectively, were analyzed to determine the degree of change in crystallinity with respect to the pressure (refer to FIG. 4).

It can be seen that the characteristic peaks of the halloysite nanoparticles passed at a pressure of 10,000 psi were almost preserved and the crystal structures of the halloysite nanoparticles passed at a pressure of 20,000 psi were maintained. As can be seen from the SEM images obtained at each condition, the degree of grinding and the change in crystallinity coincide with each other Analysis of the Average Particle Sizes of Halloysite Nanoparticles at Various Pressures with Respect to the Number of Passes Examining the average particle sizes of the halloysite nanoparticles at each pressure with respect to the number of passes, the minimum particle size of the halloysite nanoparticles was reduced when the pressure was increased, and the change in the particle size was significantly reduced after passing more than 6 times.

That is, it is considered that due to the nature of the high pressure grinding process, the nanotubes with a larger mass were ground and then the nanotubes with an intermediate mass were ground only when the collision occurred several times.

While the nanotubes were not ground by one collision in the case where the mass of the nanotubes was not sufficiently large, the nanotubes were finally ground due to cracks or fatigue occurring in the nanotubes, which coincides with the results obtained from the XRD patterns and SEM images.

However, sufficiently small nanotubes were not ground even after passing 48 times but maintain their shape and particle size. Moreover, the nanotubes showed a distinct bimodal particle size distribution after passing 24 times at a pressure of 10,000 psi, differently under the pressure of 20,000 psi or 30,000 psi.

It is believed that the reason for this is that the impact energy was also reduced as the pressure was reduced, and the reason the nanoparticles having a particle size of 0.2 µm or less were not seen until passing 12 times and showed a distinct bimodal particle size distribution after passing 24 times is that the nanoparticles were destroyed by fatigue strength due to stress accumulation.

Figure 6:
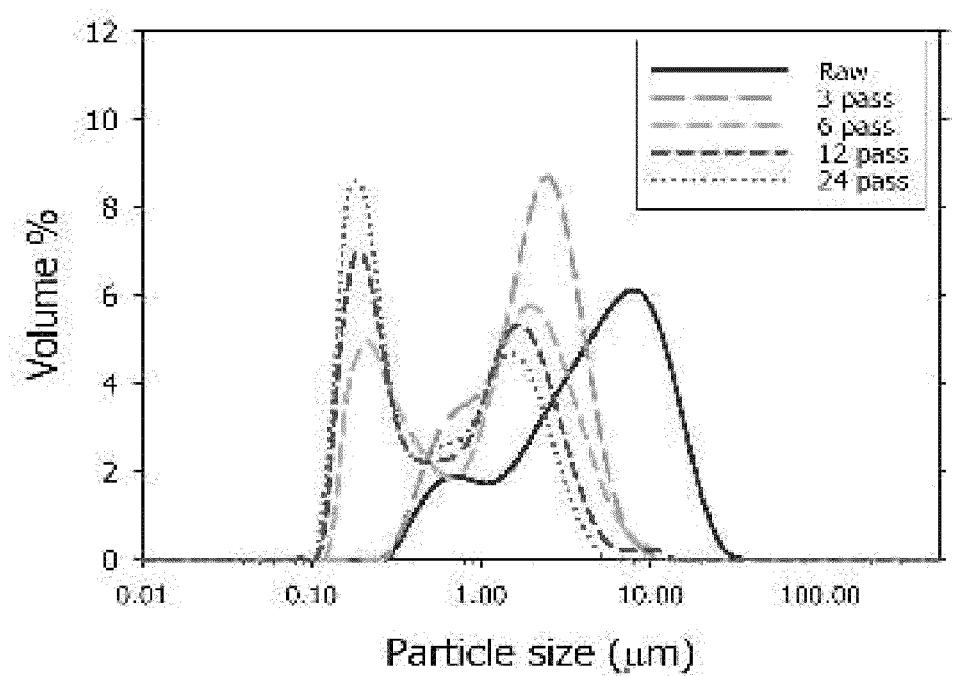
FIG. 6 shows the average particle size distributions of halloysite nanoparticles measured after injecting a 3% halloysite colloidal solution through a microfluidizer at a pressure of 30,000 psi with respect to the number of passes.

When the colloidal solution at a concentration of 3% was injected at a pressure of 30,000 psi, the average particle size was gradually reduced as the number of passes was increased and the nanoparticles showed a distinct bimodal particle size distribution after passing 6 times (refer to FIG. 6). The nanoparticles having a particle size of 10 µm or more disappeared after passing 3 times, and the nanoparticles having a particle size of 5 µm or more remained in a very small amount after passing 12 times and were finely ground after passing 24 times.

Figure 7:
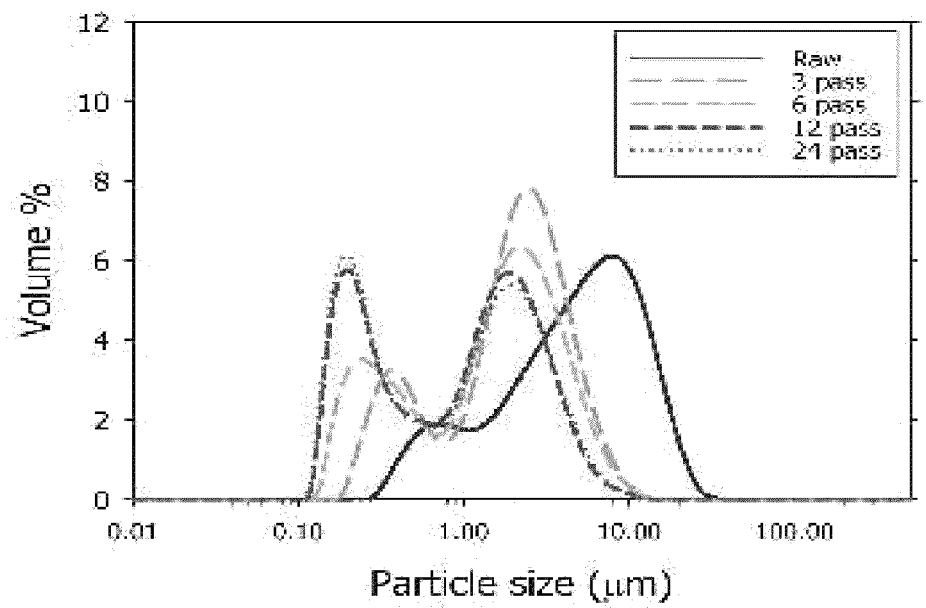
FIG. 7 shows the average particle size distributions of halloysite nanoparticles measured after injecting a 3% halloysite colloidal solution through a microfluidizer at a pressure of 20,000 psi with respect to the number of passes.

When the colloidal solution at a concentration of 3% was injected at a pressure of 20,000 psi, the average particle size was gradually reduced as the number of passes was increased and the nanoparticles showed a distinct bimodal particle size distribution after passing 3 times (refer to FIG. 7). The nanoparticles having a particle size of 10 µm or more disappeared after passing 3 times, and the nanoparticles having a particle size of 5 µm or more remained about several percent after passing 24 times.

The nanoparticles having a central peak at 0.2 µm and 2 µm showed a distinct bimodal particle size distribution with similar volume fraction after passing 12 times and 24 times. The halloysite nanoparticles having a particle size of 5 µm or less were prepared after passing through the microfluidizer about 12 times at a pressure of 20,000 psi, but the volume fraction was somewhat reduced compared to the pressure of 30,000 psi.

While it can be seen that most of the large nanoparticles were ground after passing about 12 times at a pressure of 20,000 psi and were no longer ground, the nanoparticles having a particle size of 2 µm or more were still present, which is considered that the grinding force was reduced because the number of nanoparticles in the entire colloidal solution was increased to allow the nanoparticles to collide with each other. Moreover, it is considered that the nanoparticles having a smaller particle size can be finely ground when the entire grinding energy is further increased.

Figure 8:
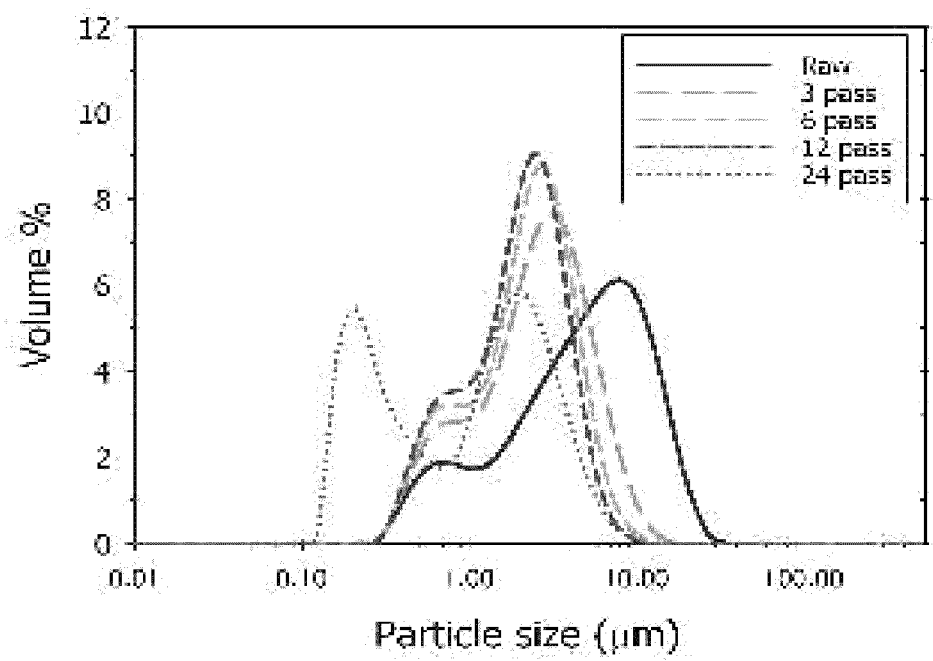
FIG. 8 shows the average particle size distributions of halloysite nanoparticles measured after injecting a 3% halloysite colloidal solution through a microfluidizer at a pressure of 10,000 psi with respect to the number of passes.

When the 3% halloysite colloidal solution was injected through the microfluidizer at a pressure of 10,000 psi, the nanoparticles showed a distinct bimodal particle size distribution after passing 24 times, differently under the pressure of 20,000 psi or 30,000 psi (refer to FIG. 8), which was because the impact energy was linearly reduced as the pressure was reduced.

It is assumed that the reason the nanoparticles having a particle size of 0.2 µm or less were not seen until passing 12 times and showed a distinct bimodal particle size distribution after passing 24 times is that the nanoparticles were destroyed by fatigue strength due to stress accumulation. Most of the nanoparticles having a particle size of 10 μm or more were ground after passing 3 times. The halloysite nanoparticles having a particle size of 5 μm or less could be prepared after passing through the microfluidizer 24 times even at a pressure of 10,000 psi.

Figure 9:
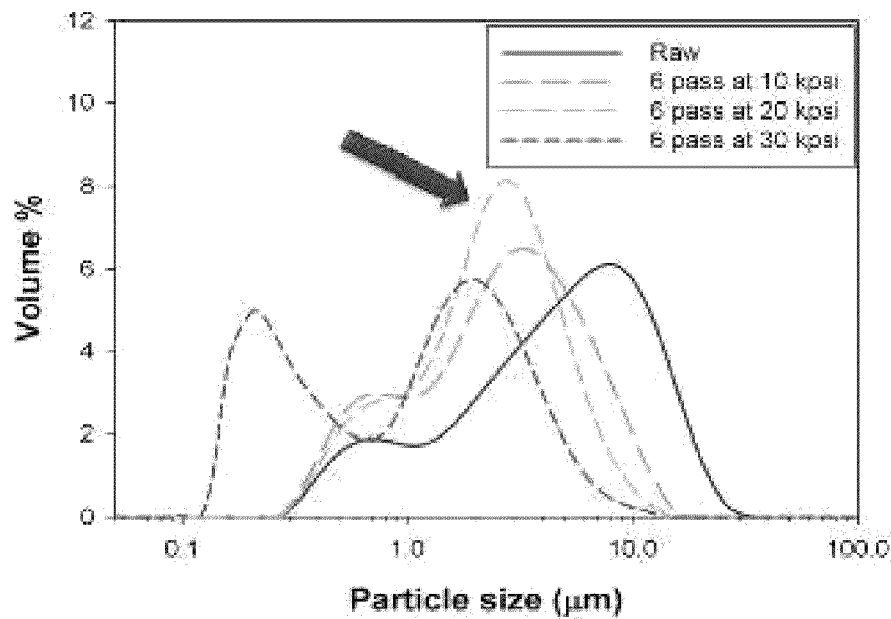
FIG. 9 shows the average particle size distributions of halloysite nanoparticles measured after passing a 3% halloysite colloidal solution through a microfluidizer 6 times at a pressure of 10,000 psi, 20,000 psi, and 30,000 psi, respectively.

To determine the conditions for preparing the halloysite nanoparticles having a particle size of 10 μm or less from the above-described test results, the halloysite colloidal solution was passed through the microfluidizer 6 times at each pressure. As a result, the formation of the particles having a submicron particle size was minimized at a pressure of 20,000 psi, and most of the nanoparticles having a particle size of 10 μm or more were ground (refer to FIG. 9).

Figure 10:
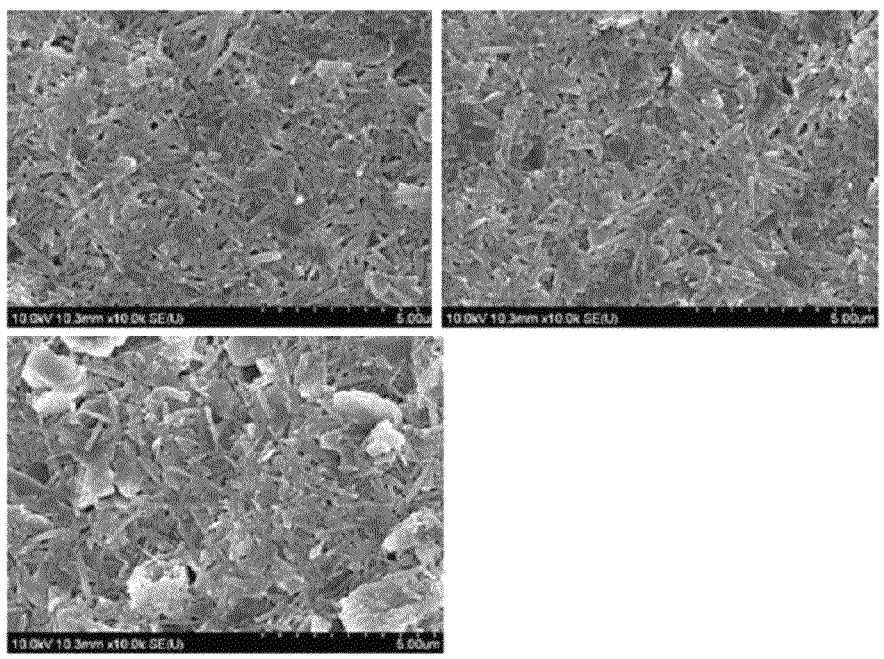
FIG. 10 shows TEM images of the shapes of halloysite nanoparticles obtained after passing a 3% halloysite colloidal solution through a microfluidizer 6 times at a pressure of 10,000 psi, 20,000 psi, and 30,000 psi, respectively.

Moreover, as can be expected from the results of the particle size distributions of the FE-SEM images showing the shapes of the nanoparticles, it was possible to obtain the halloysite nanopowders having a particle size of 10 μm or less with the tubular shape when the halloysite nanotubes were ground at a pressure of 20,000 psi (refer to FIG. 10).

The particle size was reduced when the pressure was increased and, especially, the small nanoparticles agglomerated together at a pressure of 30,000 psi to form large agglomerates. Therefore, it was finally confirmed that the halloysite nanotubes can be optimally ground at a pressure of 20,000 psi 6 times.

EXAMPLE 2

Figure 11:
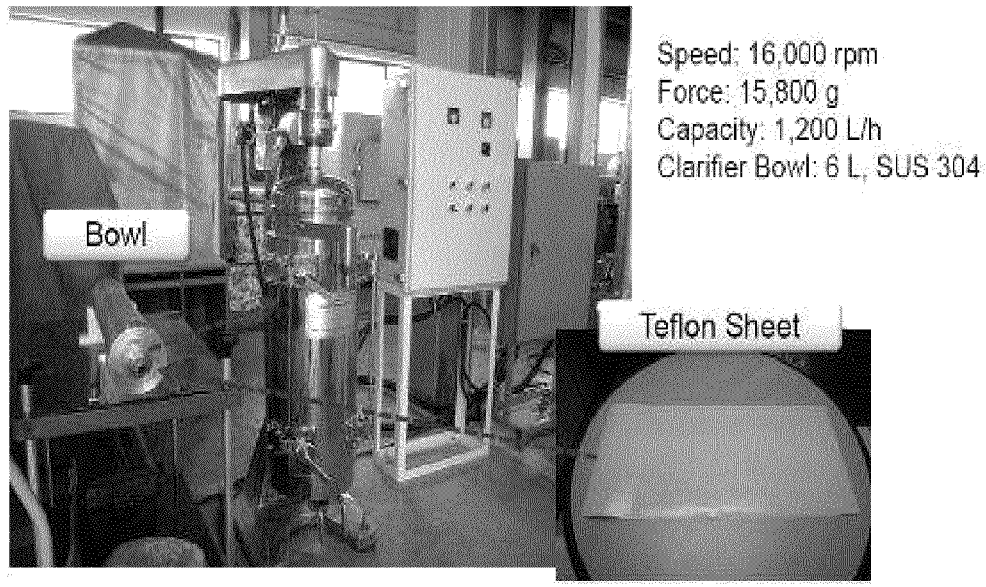
FIG. 11 shows a continuous centrifuge in which a bowl is lined with a Teflon sheet to select halloysite nanopowders having a desired size.

Analysis of Halloysite Nanoparticles Selected After Lining Centrifuge Tube with Teflon Sheet A continuous centrifuge (manufactured by Hanil Science Medical Co., Ltd. Model J-1050) used in the present invention could apply a centrifugal force that was 15,800 times the force of gravity at a maximum speed of 16,000 rpm and a flow rate of 1,200 L/h. The centrifuge bowl was lined with a Teflon sheet to easily collect nanoparticles after operating the centrifuge (refer to FIG. 11).

A 10 wt % (200 g/2 L) halloysite suspension was stirred for about 1 hour to be subjected to ultrasonic treatment, and the resulting suspension was passed through a microfluidizer at a pressure of 20,000 psi 6 times and then diluted to 1 wt % while maintaining the pH of the suspension at 10. Then, the solid and liquid phases were separated by the centrifuge and sampled (flow rate 6 lpm; centrifugal speed 5,200 rpm) by dividing the solid content from an inlet of the centrifuge at intervals of 14 cm.

Figure 12:
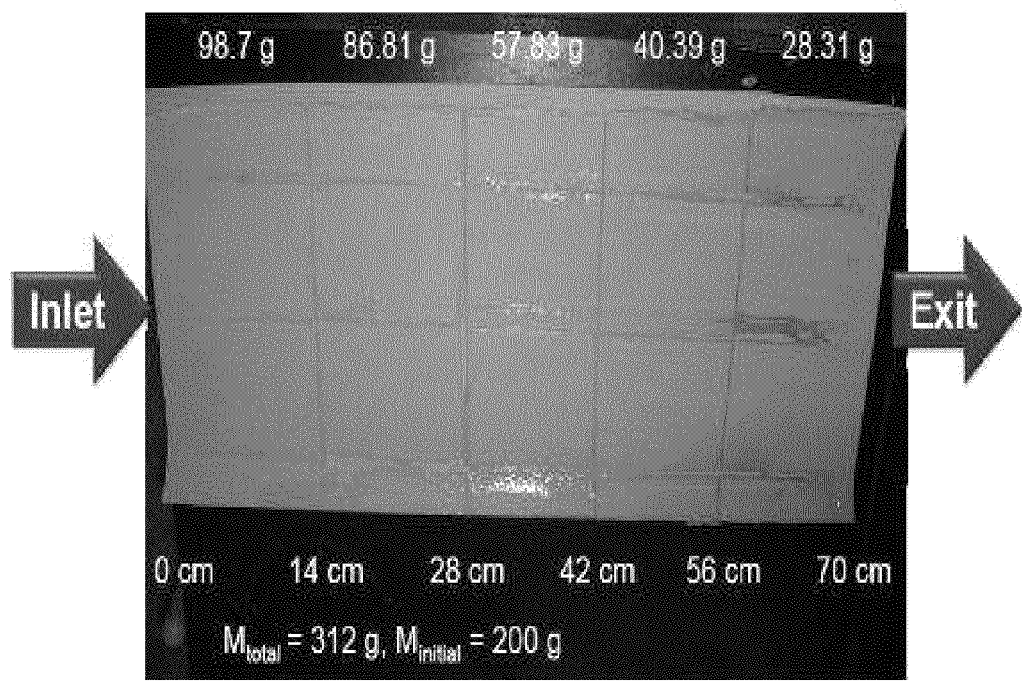
FIG. 12 is an image showing the expression of halloysite nanoparticles collected on the Teflon sheet after operation of the centrifuge of FIG. 11.

Dried halloysite nanotubes with a mass of 200 g, added before the centrifugation according to the particle size determination process by the continuous centrifugation, absorbed water while being dispersed in distilled water for the centrifugation, and thus the mass was increased to 312 g. The horizontal lines on the Teflon sheet were formed by supports provided in the bowl as a centrifuge rotor (refer to FIG. 12).

Figure 13:
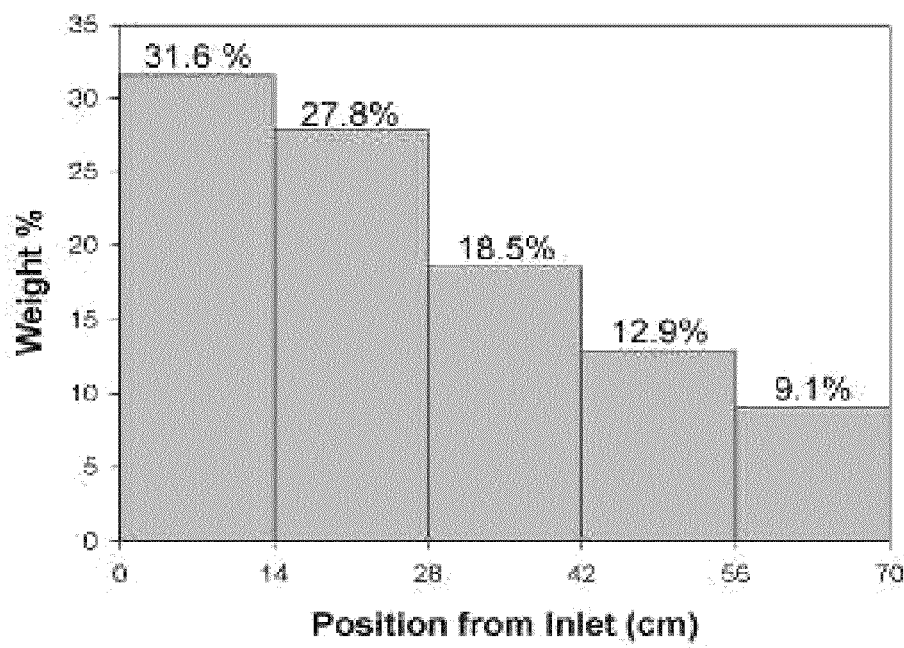
FIG. 13 shows the yields of halloysite nanoparticles by the continuous centrifugation.

Examining the yields by the continuous centrifuge from the results, it can be found from the samples collected on the Teflon sheet in the region up to 28 cm from the inlet that it was possible to collect nanoparticles having a particle size of 0.3 μm or more at a yield of 59.4% (31.6%+27.8%) (refer to FIG. 13).

Figure 14A:
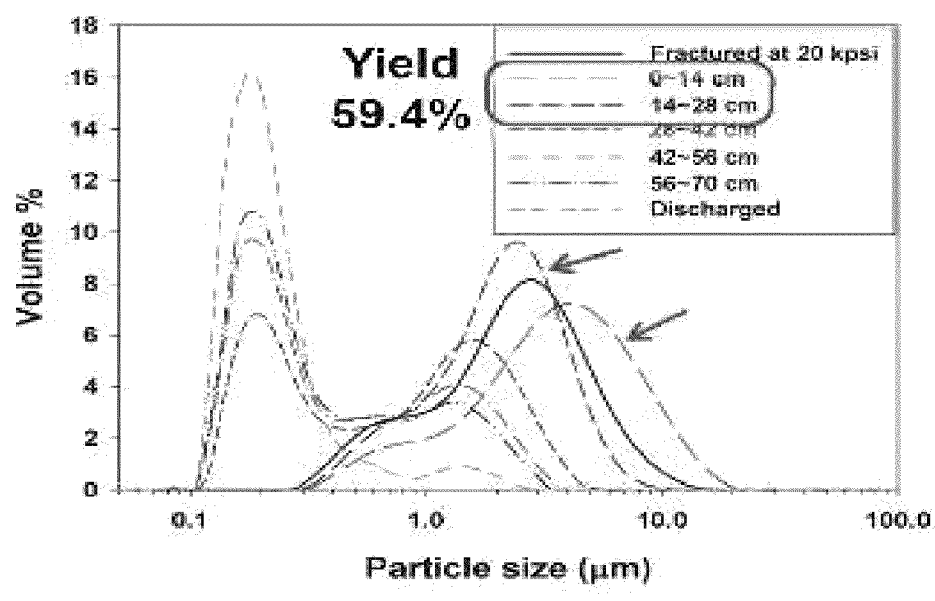
FIG. 14A shows the particle size distributions of halloysite nanoparticles collected at predetermined intervals from an inlet of the continuous centrifuge.

When the centrifugation was carried out at a flow rate of 3.5 L/min and a speed of 6,000 rpm, a lot of nanoparticles having a particle size of 0.3 μm or less were present in the region of 0 to 28 cm, indicating the need for an increase in the flow rate. Examining the particle size distributions of the nanoparticles collected from the inlet of the centrifuge revealed, when the centrifugation was carried out at a flow rate of 6 L/min (lpm) and a speed of 5,200 rpm, that most of the nanoparticles having a particle size of 0.3 μm or less in the region up to 28 cm disappeared (refer to FIG. 14A).

Here, the particle size was measured by laser diffraction using a particle size analyzer (PSA, Malvern), and thus it is a light scattering equivalent diameter indicating the particle diameter assuming that the particle is a sphere, not the actual tubular shape.

Figure 14B:
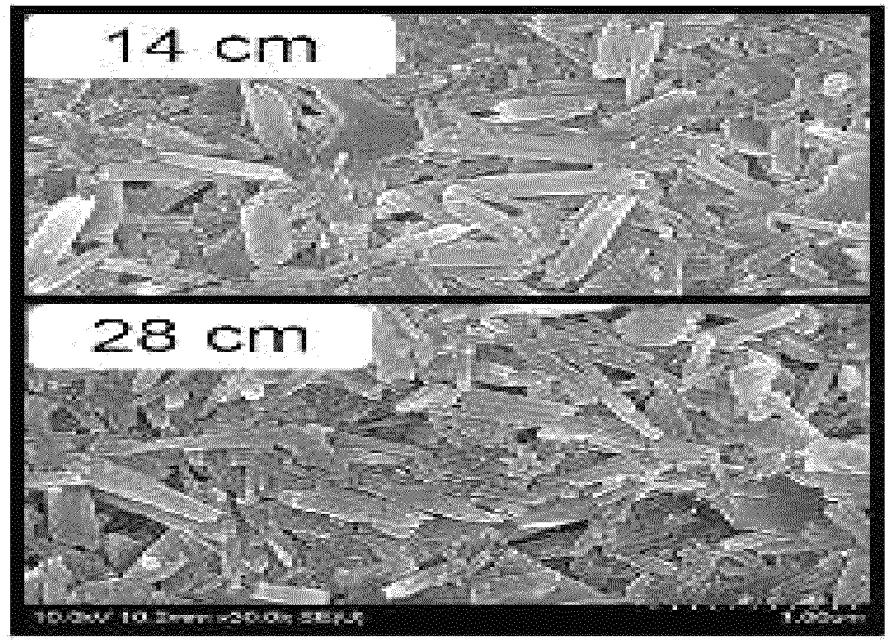
FIG. 14B shows TEM images of halloysite nanoparticles collected in the regions of 0 to 14 cm and 14 to 28 cm from an inlet of a microfluidizer.

It is believed that the reason the volume percent (vol %) of large particles was increased in the region of 0 to 14 cm is that it seems that the amount of large particles among the whole particles was relatively increased, which is seen as the vol % was increased but the absolute quantity was the same. Examining the shapes of the nanoparticles, it was found that the halloysite nanoparticles having a tubular shape were present in the region up to 28 cm from the inlet (refer to FIG. 14B).

COMPARATIVE EXAMPLE 1

Fine Grinding Process of Halloysite Nanotubes Using a Bead Mill

Halloysite nanotubes were finely ground using a bead mill (Ultra Apex Mill, manufactured by Kotobuki Ind. Co., Ltd., Model UAM-015) under operating conditions such as zirconia bead sizes (15, 30, 100, and 300 μm), pulp concentration [3% (WN) or 6 g/200 mL], rotor speeds (10, 20, 40, 60, and 80 Hz), milling times (10 to 60 min), and retention time in the jacket (100 ml/min, controlled by the slurry flow rate). Here, the rotational speed of the rotor was expressed as frequency. Frequency 10 Hz corresponded to a rotational speed of 830 rpm and a circumferential speed of 1.9 m/s, and thus the bead mill could be operated up to a circumferential speed of 15.2 m/s at a maximum frequency of 80 Hz.

Figure 15A:
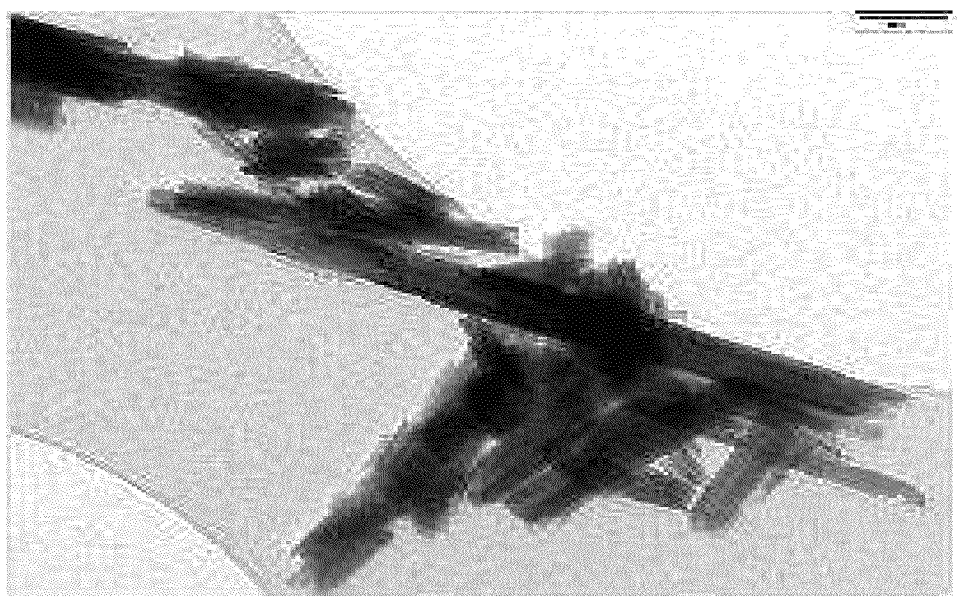
FIG. 15A shows a TEM image of raw halloysite nanotubes.
Figure 15B:
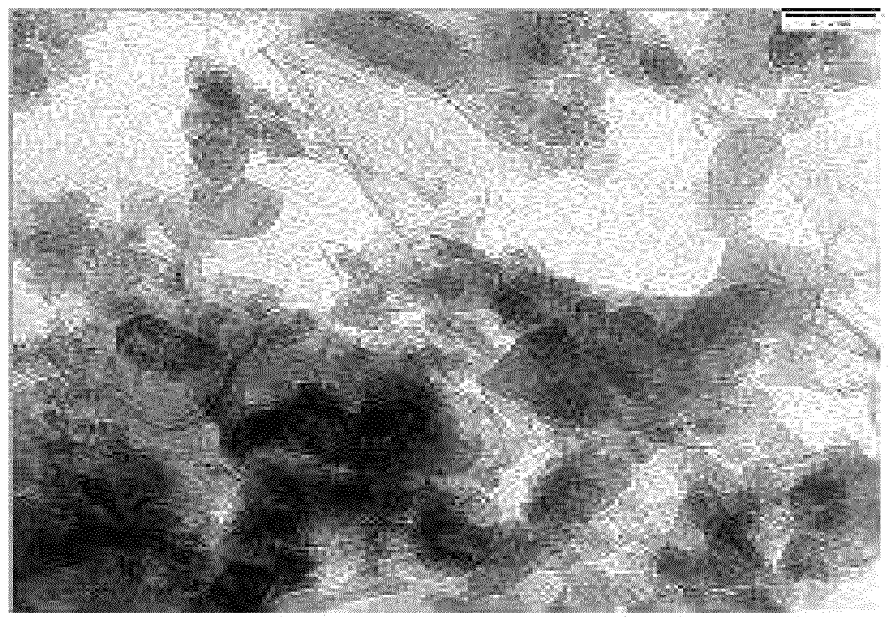
FIG. 15B shows a TEM image of halloysite nanoparticles ground by a conventional bead mill with a bead size of 0.1 mm at a rotor speed of 60 Hz, at a concentration of 6 g/200 mL, and a milling time of 10 minutes.

The TEM images show that most of the nanoparticles were ground into a flake shape and there were relatively few nanoparticles with a tubular shape, which is assumed that the nanoparticles were broken into small pieces due to high energy during collision with the beads (refer to FIGS. 15A and 15B). Moreover, it is decided that the particle size of the beads is more than 10 times that of the nanoparticles, and thus only the collision, compressive, and shear stresses mainly act on the nanoparticles, but the bending stress that can cut the tubular or rod-like nanoparticles is difficult to act on the nanoparticles, which had a significant effect on the results.

Figure 16:
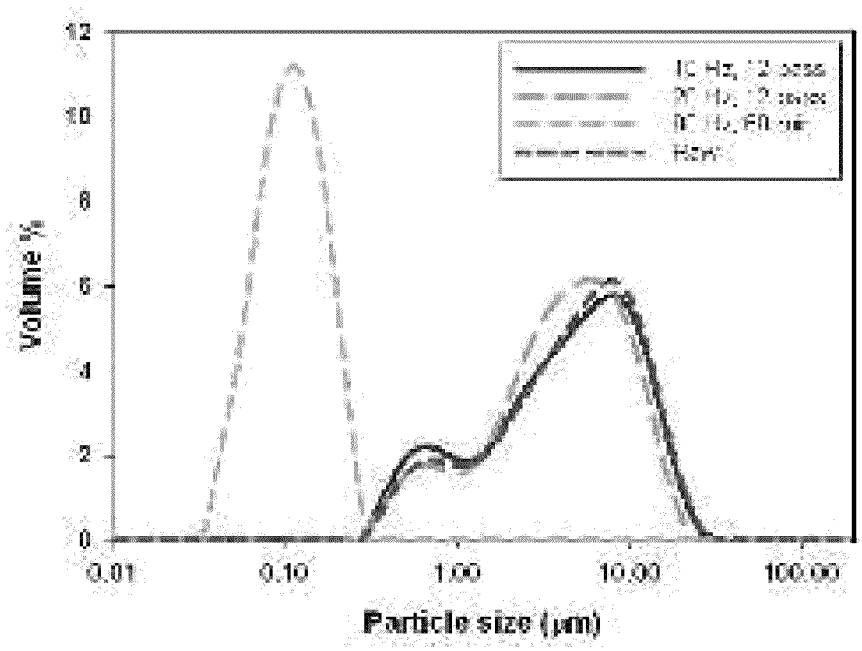
FIG. 16 shows the particle size distributions of halloysite nanoparticles measured after grinding in the conventional bead mill at various rotor speeds.

Since the number of nanoparticles with a tubular shape, which were finely ground at a rotor speed of 60 Hz using beads having a diameter of 0.1 mm, was small, the grinding process was carried out at 10 Hz and 20 Hz while reducing the grinding energy. As a result, there was a little change in the particle size distribution at 20 Hz, and the grinding efficiency was significantly reduced compared to 80 Hz (refer to FIG. 16).

Therefore, it was revealed that the above-described bead milling method was an unsuitable method for maintaining the tubular shape of the halloysite nanoparticles and reducing the length to a submicron range.

COMPARATIVE EXAMPLE 2

Selection of Particle Sizes of Halloysite Nanoparticles by Batch-Type Centrifugation Polyethylene glycol (PEG) with a specific gravity of 1.11 and a dynamic viscosity of 4.3 cSt was used as a dispersion medium. The specific gravity of halloysite nanoparticles was about 2.0, and the nanoparticles having a particle size of 5 μm or less were to be separated. The centrifuge (manufactured by Hanil Science Medical Co., Ltd. Model Continent R) used in the test could be operated at a maximum speed of 8,000 rpm.

Here, the centrifugal force applied to the samples was about 13,952 times the force of gravity. A halloysite colloidal solution at a concentration of 10%(w/v) was stirred with ultrasonic waves for about 1 hour and centrifuged at a predetermined rotational speed for 10 minutes, and then the supernatant was separated to measure the particle size distributions.

Figure 17:
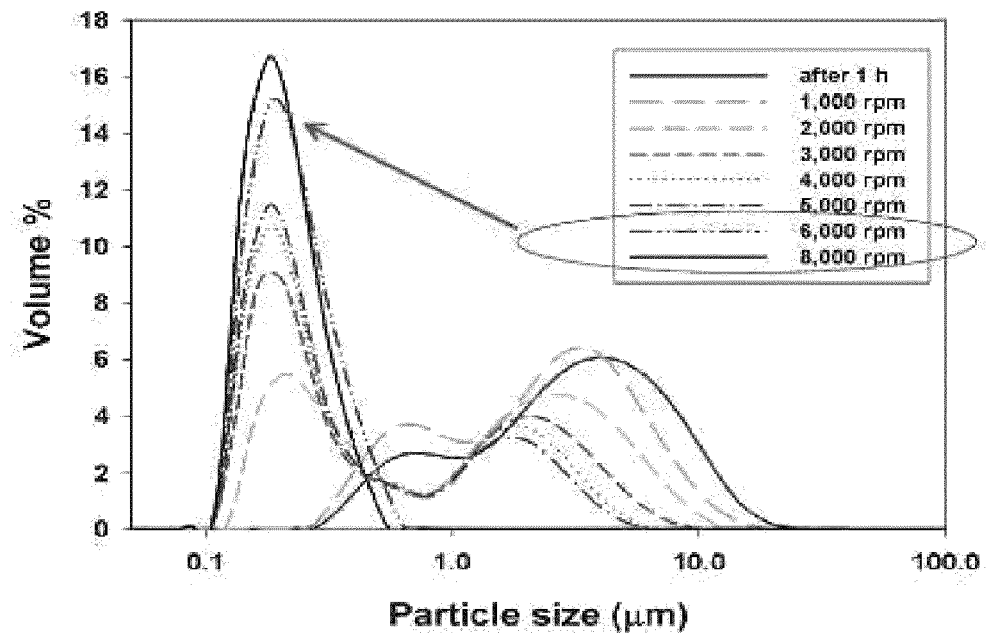
FIG. 17 shows the particle size distributions of halloysite nanoparticles measured after separation using a typical batch-type centrifugation method at various rotational speeds.
Figure 18:
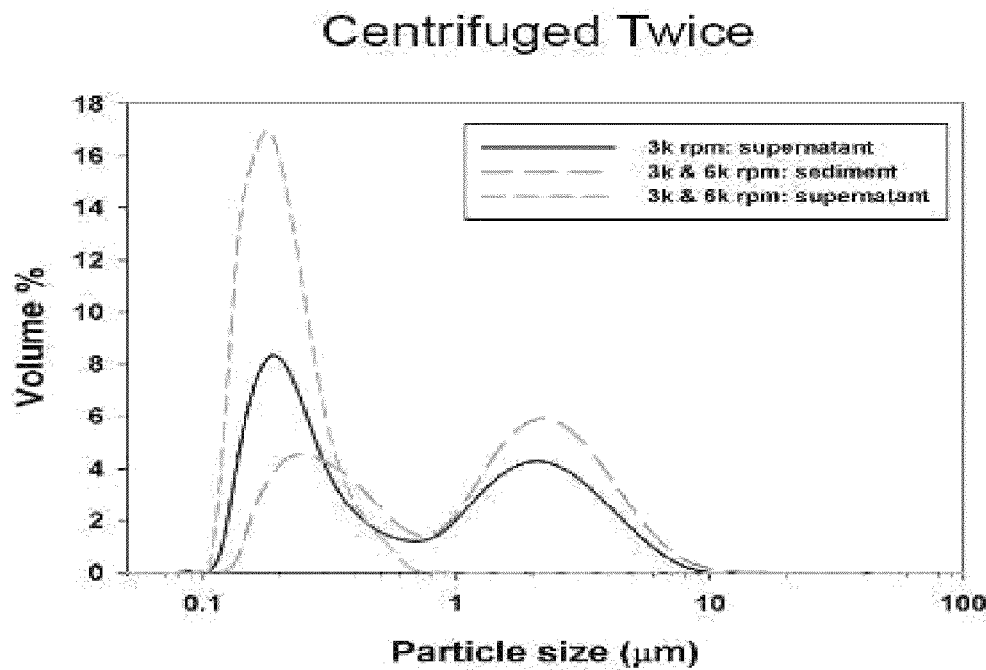
FIG. 18 shows the particle size distributions of halloysite nanoparticles measured after centrifugation at a rotational speed of 3,000 rpm and 6,000 rpm, respectively.

The nanoparticles having a small particle size could be separated from the supernatant at a rotational speed of 6,000 rpm or more by the conventional batch-type centrifugation method (refer to FIG. 17). To remove the particles having a submicron size, the halloysite colloidal solution was first centrifuged at a rotational speed of 3,000 rpm, and the precipitate was centrifuged again at a rotational speed of 6,000 rpm. As a result, the nanoparticles having a small particle size were still present, and the second precipitate showed a distinct bimodal particle size distribution in which the small and large nanoparticles were mixed (refer to FIG. 18).

Therefore, it was confirmed that it was difficult to effectively separate the small particle size group from the large particle size group by the batch-type centrifugation method.

As described above, according to the method for preparing the microtubular halloysite nanopowders of the present invention, it is possible to minimize the formation of particles having a submicron size and grind most nanoparticles having a particle size of 10 μm or more. Moreover, according to the method of the present invention, it is possible to cut the halloysite nanotubes to have a tubular shape and separate the small particle size group from the large particle size group. Therefore, the halloysite nanopowders prepared by the method according to the present invention can be used as a container or carrier for nanostructures and organic materials such as drugs, cosmetics, agricultural chemical materials, etc. Moreover, as the halloysite nanopowders are environmentally-friendly nanomaterials that can maintain the efficacy for a long time, the halloysite nanopowders can be used as high value-added materials in many industrial fields.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A method for preparing a microtubular halloysite nanopowder, comprising cutting a halloysite nanotube at 15,000 to 25,000 psi pressure.

2. The method of claim 1, wherein the cutting of the halloysite nanotube comprises continuously grinding the halloysite nanotube 3 to 9 times.

3. The method of claim 1, wherein the microtubular halloysite nanopowder has a length of 1 to 10 μm with a tubular shape.

4. The method of claim 1, wherein the microtubular halloysite nanopowder has a length of 1 to 5 μm with a tubular shape.

5. The method of claim 1, wherein the halloysite nanotube cut at a high pressure is in the form of a 3 to 10 wt % colloidal solution.

6. The method of claim 1, further comprising selecting a halloysite nanopowder having a desired shape from the cut halloysite nanotubes using a continuous centrifuge.

7. The method of claim 6, wherein the microtubular halloysite nanopowder has a length of 1 to 5 μm with a tubular shape.

8. The method of claim 6, wherein the selecting of the halloysite nanopowder comprises lining a centrifuge tube with a PTFE (Polytetrafluoroethylene) sheet and operating the centrifuge.

* * * * *